(12) United States Patent
Rice et al.

(10) Patent No.: US 7,311,848 B2
(45) Date of Patent: Dec. 25, 2007

(54) SEPARATION APPARATUS

(75) Inventors: Matthew Rice, Göteborg (SE); Hans Wijk, Göteborg (SE)

(73) Assignee: AKZO Nobel N. V., Arnhem (NL)

( * ) Notice: Subject to any disclaimer, the term of this patent is extended or adjusted under 35 U.S.C. 154(b) by 355 days.

(21) Appl. No.: 10/987,183

(22) Filed: Nov. 15, 2004

(65) Prior Publication Data

US 2005/0103098 A1    May 19, 2005

(51) Int. Cl.
*B04B 5/12* (2006.01)
*G01N 33/34* (2006.01)

(52) U.S. Cl. ............ 210/739; 210/781; 210/330; 210/360.1; 162/49; 162/55; 162/263

(58) Field of Classification Search .......... 210/781, 210/330, 739, 745, 780, 360.1; 73/64.43; 162/1, 49, 55, 232, 263
See application file for complete search history.

(56) References Cited

U.S. PATENT DOCUMENTS

| | | |
|---|---|---|
| 1,363,699 A | 12/1920 | Albert |
| 3,152,078 A | 10/1964 | Lavanchy |
| 3,501,414 A | 3/1970 | Mueller |
| 4,441,960 A | 4/1984 | Karnis et al. |
| 5,618,335 A | 4/1997 | Pink et al. |
| 5,993,674 A * | 11/1999 | Rolchigo et al. .......... 210/780 |

FOREIGN PATENT DOCUMENTS

FR    1 326 779 A    5/1963

OTHER PUBLICATIONS

PTO 07-4735-Translation of French Patent No. 1.326. 779 which published Apr. 1, 1963.*
International Search Report, completed Feb. 8, 2005.

* cited by examiner

*Primary Examiner*—David A Reifsnyder
(74) *Attorney, Agent, or Firm*—David J. Serbin; Robert C. Morriss

(57) ABSTRACT

The present invention relates to a method of monitoring a liquid fluid mixture and a system carrying out the method. The invention also relates to the use of the system for monitoring liquid fluid mixtures.

14 Claims, 4 Drawing Sheets a)

b)

c)

d)

SEPARATION APPARATUS

The present invention relates to a monitoring system, a method of characterising a liquid fluid mixture or at least one component in said mixture by means of the monitoring system, and the use thereof for various applications.

BACKGROUND OF THE INVENTION

Separation methods such as centrifugation and filtration have been used for a long time. Centrifugation is often a suitable method for thickening a liquid-solid mixture or for removing unwanted particles from a liquid-solid mixture before further use or treatment. Separation may also be carried out to avoid unwanted environmental problems or fire hazards.

U.S. Pat. No. 3,152,078 discloses a stationary-walled centrifuge for separating phases, especially for removing water and/or sand from crude petroleum oil. This centrifuge provides for high volume throughput and thus short retention time. However, U.S. Pat. No. 3,152,078 is silent on monitoring a production process from which a sample is withdrawn for subsequent analysis.

Filtration has been particularly used in the separation of wood fibre and filler materials from a paper furnish. However, it has not been possible to separate filler material and fibre fines from colloidal components due to the similar particle sizes. Furthermore, it has been shown that colloidal components tend to be retained in the fibre mat (cake) formed on the filter. Filtration devices are also often prone to fouling and require regular cleaning.

The intention of the present invention is to provide a convenient, inexpensive system monitoring a liquid fluid mixture which may be e.g. a process stream withdrawn from a production process, a tank containing e.g. a pulp suspension or the like, or monitoring at least one component in the liquid fluid mixture while avoiding the drawbacks of the prior art. Particularly, the invention intends to provide a system for monitoring a production process, e.g. a paper-making process. A further object of the invention involves providing a worked-up sample in which characterisation and measurements can be accurately performed in the substantial absence of separated interfering substances that would otherwise make the measurements less accurate. The invention further involves a method of optimally running a production process, particularly a paper-making process.

THE INVENTION

The present invention relates to a method of monitoring a fluid liquid mixture or at least one component therein comprising pressurising and supplying the fluid liquid mixture to a separation apparatus comprising at least two rotatable discs defining at least one space between said discs, and means for withdrawing a dense fraction of the liquid fluid mixture from the perimeter of the discs. The discs are arranged to a rotatable axis defining within it at least one bore fluidly communicating with the space or spaces. The bore(s) has at least one outlet for removing a light fraction of the liquid fluid mixture. The pressurised liquid fluid mixture is supplied to the apparatus and subjected to centrifugal forces in the space or spaces by the rotating discs, such that a light fraction of the liquid fluid mixture is pressed to the bore for removal thereof, and a dense fraction of the liquid fluid mixture is pressed to the perimeter of the discs for withdrawal thereof, guiding the withdrawn light fraction to an analyser to characterise the light fraction or at least one component contained therein.

The present invention also relates to a monitoring system comprising; a separation apparatus comprising at least two rotatable discs defining at least one space between said discs, means for pressurising and supplying a liquid fluid mixture to the separation apparatus, means for withdrawing a dense fraction of the liquid fluid mixture from the perimeter of the discs, said discs being arranged to a rotatable axis defining within it at least one bore fluidly communicating with said at least one space, said at least one bore having at least one outlet for removing a light fraction of the liquid fluid mixture; said system further comprising an analyser connected to said separation apparatus to guide the light fraction from the outlet to the analyser to characterise said light fraction or at least one component therein.

The characterisation of the light fraction or the components therein making up the analysed liquid fluid mixture may comprise e.g. the determination of properties such as the particle size, charge (e.g. surface charge), particle size distribution, or the concentration of a particular component, as well as pH, charge or other parameter of the fraction.

The rotatable axis on which the rotatable discs are arranged may be driven by any means, e.g. a motor.

By the term "bore" is meant to include any hole, cavity, or channel capable of leading a fluid along the interior of the axis in which it is located.

By "liquid fluid mixture" or "fluid" is meant to include liquid materials, that flows or are pumpable, such as solutions which may include solids, colloids, dissolved and/or entrained gases such as air, e.g. colloidal solutions, mixtures of liquids, solutions comprising dissolved or dispersed solids, suspensions, slurries of e.g. sludge or pumpable sediment, emulsions, froth, pumpable gel-like materials, thixatropic material (fluid when agitated but jellylike when at rest), and mixtures thereof.

The dense fraction of the liquid fluid mixture which may be e.g. a thickened feed of a liquid-solid mixture, is obtained at the perimeter of the rotating discs, which preferably is recirculated into the separation apparatus for further fractionation.

The fluid to be fractionated is subjected to centrifugal forces through shear forces when it reaches the space between the discs. These forces are developed between the discs. The shear forces are produced at the surface of the rotating discs which result in a rotational flow field generating the centrifugal forces which in turn press the fluid towards the perimeter of the discs. If the development of boundary layers within the fluid present between the discs occurs rapidly, the angular velocity of the fluid between the discs will be approximately the angular velocity of the rotating discs. For a rotational flow field, a centrifugal force is generated. The centrifugal force acting on a fluid element ($F_c$) is approximately proportional to the square of the angular velocity ($\omega$) of the rotating discs multiplied by the radius (r), written $F_c \propto r\omega^2$.

The centrifugal field of force generated in the fluid between the discs produces a radial pressure drop $\Delta P$ across each disc from the perimeter to the outlet of the bore(s) that must be overcome such that a light fraction of the fluid can be pressed to said outlet and withdrawn therefrom. Thus, the pressure of the fluid supplied to the apparatus, here called $P_{bulk}$, (cf. reference sign 11 of FIG. 2), which usually can be appreciated to be approximately equal to the pressure at the perimeter, must be greater than the radial pressure drop $\Delta P$ generated across the rotating discs and the outlet of the bore, i.e. $P_{bulk} > \Delta P$, where $\Delta P = P_{perimeter} - P_{bore\ outlet}$, and $P_{perimeter}$ (cf. reference sign 4 of FIG. 2) and $P_{bore\ outlet}$ (cf. reference sign 10 of FIG. 2) are the fluid pressures at the perimeter and at the bore outlet respectively. Preferably, $P_{bulk}$ is from about 1 μPa to about 10 MPa, more preferably from about 1 Pa to about 10 MPa, and most preferably from about 1 kPa to about 0.5 MPa, provided that $P_{bulk} > \Delta P$. The selection of $P_{bulk}$ must be based on a plurality of parameters such as type of liquid mixture to be separated, $\Delta P$ generated, which is a function of inter alia the disc diameters and the angular velocity of the rotating discs, etc. The magnitude of $P_{bulk}$ affects the hold-up time of a sample to be fractionated. If $P_{bulk}$ is too high, the hold-up time in the apparatus will be so short that a desirable fractionation cannot be performed. Cavitation may also occur if $P_{bulk}$ is too high resulting in impaired fractionation. On the contrary, if a too low $P_{bulk}$ is applied but still greater than $\Delta P$, the hold-up time becomes undesirably long and only a small fraction is collected. However, $P_{bulk}$ can preferably be selected to be slightly greater than $\Delta P$ for fractionating liquid fluid mixtures containing sensitive components which at higher $P_{bulk}$ would be liable to disruption. By forcing the flow of fluid through the generated field of force, continuous centrifugal separation can be achieved.

A means is preferably provided such that the liquid fluid mixture in and/or around the discs can be supplied and pressurised in order to force a flow of fluid through the outlet of the bore while the discs are rotating. Such means may be a separate part which can be arranged externally, i.e. outside the perimeter and/or housing of the separation apparatus, or be an integral part of the separation apparatus arranged to be driven e.g. by a motor driving the rotating axis, or other means. Preferred means for supplying and pressurising the liquid fluid mixture include e.g. a pump such as a centrifugal pump, or a monopump, preferably arranged externally along a feed line connected to the separation apparatus. According to one embodiment, the pressure can be applied by placing the apparatus in a tank or the like, e.g. a large storage tank where the $P_{bulk}$ required is obtained from the static fluid pressure in the tank. Still further means could include placing the separation apparatus in pipes or any other suitable pressurised construction. The pressure applied to the fluid can be controlled e.g. by a valve which can be arranged downstream of an outlet for a dense fraction of the fluid.

The separation apparatus can be either open, or closed by a suitable housing. However, if a housing, e.g. a bowl, is utilised, the housing is preferably stationary and does not itself subject the material to centrifugal forces. According to one embodiment, the separation apparatus has a surrounding housing comprising an inlet fluid feed and an outlet for a dense fluid, e.g. a thickened fluid fraction, arranged at such locations that turbulence or disruption of the flow regime within the rotating discs is minimised. Preferably, at least one outlet is provided at the perimeter of each pair of discs for efficient withdrawal of a dense fluid fraction. In case the apparatus is open, the perimeters of the discs define the outer boundary thereof. In such embodiment, the open perimeter(s) of the discs function as means for withdrawing a dense fraction of the fluid.

The separation apparatus preferably is a centrifuge, most preferably a continuous centrifuge, in which a fluid can be revolved about the axis at such a number of revolutions per unit of time that the apparent weight of its constituents increases to a point where the constituents tend to concentrate in strata similar to gravity-induced separation based on relative densities.

Between each pair of discs, a means is preferably provided to allow fluid to be withdrawn at the outlet of the bore. Preferably, a light fraction of the fluid is withdrawn from the space between adjacent discs somewhere trough at least one aperture enabling fluid communication between the spaces between the discs and the bore in the axis.

However, according to one embodiment, apertures may also be provided in the discs fluidly communicating with the bore of the axis through cavities in the discs. The apertures may be provided in the discs at different distances from the axis to lead fluid towards the bore via the cavities in the discs for withdrawal thereof.

Preferably, from about 0.0000001 to about 25, more preferably from about 0.000005 to about 10, and most preferably from about 0.05 to about 5% by volume of a liquid fluid mixture is withdrawn from a production process, e.g. from a tank, a process stream or the like and supplied to the monitoring system. The liquid fluid mixture, usually being a process stream may be derived from e.g. a pulp suspension in a papermaking process.

Preferably, from about 0.1 to about 15, more preferably from about 1 to about 10, and most preferably from about 1 to about 5% by volume of the stream supplied to the monitoring system is withdrawn from the central bore outlet of the separation apparatus for further optional working-up or is guided directly to an analyser. This ratio, i.e. the flow of the light fraction withdrawn from the separation apparatus/flow of the process stream supplied to the separation apparatus×100% by volume is commonly known as accept ratio. The remaining portion not withdrawn from the central outlet of the bore is removed from the monitoring system at the perimeter of the rotating discs. Preferably, this portion which comprises the dense fraction is preferably recirculated to the process media from which the process stream entering the separation apparatus was withdrawn. In this way, the production process is influenced only to a minimal extent due to the presence of the monitoring system.

Preferably, the sample withdrawn from the separation apparatus is further worked-up to reduce the amount of any substance which may disturb the subsequent measurements performed in the analyser.

According to one embodiment, fluid fractions from a multitude of discrete locations along the rotating discs are continuously collected in order to obtain specific density fractions of the fluid sample. Each such fraction will have different densities which subsequently can be analysed or utilised for other purpose.

According to one embodiment, a plurality of at least two separate bores which do not mutually fluidly communicate with each other are provided within the rotatable axis. Each bore fluidly communicates with the space between adjacent rotating discs of different diameters via apertures in the axis. The difference in disc diameter provides for separation of fluid fractions of varying density which thus can be withdrawn through the separate bores. Fractions of relatively dense liquid fluid mixtures are withdrawn from the space between discs of smaller diameters whereas lighter liquid fluid mixtures are withdrawn from spaces between increasingly larger disc diameters. Thus, also this embodiment can be used to withdraw specific density fractions. According to one embodiment, a further possibility to obtain different density fractions is to connect several separation apparatuses in series, wherein each subsequent apparatus in the series has smaller disc diameters. According to one embodiment, yet a further possibility to obtain different density fractions is to connect several separation apparatuses in series, wherein the rotational speed of the discs in each subsequent apparatus is lower than the rotational speed of the discs in the preceding apparatus.

The distance between the discs should preferably be optimised to the prevailing operational conditions including fluid viscosity, rotational velocity of the discs, diameter of the discs, sample type etc, to balance shear forces against slip of the fluid. Preferably the discs are arranged substantially in parallel. The distance between adjacent discs can vary as long as the fluid flow conditions are not negatively affected. Preferably, the angle $\beta$ (cf. FIG. 1) between the faces of two adjacent discs is from about 0 to about 45°, more preferably from about 0 to about 15°, and most preferably from about 0 to about 5°. Preferably, an angle $\alpha$ (cf. FIG. 1c) between the discs and the axis is from about 30° to about 120°, more preferably from about 60° to about 100°, and most preferably from about 80° to about 95°. Thus, the discs may e.g. be arranged conically to the axis.

According to one embodiment, the discs are centred, aligned and balanced to minimise vibrations. Preferably, from about 2 to about 100, more preferably from about 2 to about 10 discs are arranged to the axis. The number of discs is chosen primarily to obtain a suitable throughput and will vary from application to application. Preferably, the discs rotate the same direction to avoid turbulence which produces mixing of the fluid sample such that the centrifugal separation is destroyed. So, laminar flow conditions preferably exist within and around the rotating discs for a good separation to occur. If the discs spin too fast, turbulence can also occur. Preferably, the flow of the fluid supplied to the apparatus also is laminar. Preferably, the rotational speed of the discs is from about 500 to about 10000, more preferably from about 1000 to about 5000 rpm.

Preferably, the rotating discs are as flat and as smooth as possible. Accordingly, the discs preferably have no sharp edges and all outside edges of the discs are preferably rounded. Also the outlet at the bore is preferably smooth.

Various materials may be used for the construction of the discs, e.g. aluminium, stainless steel, glass, and plastics such as polycarbonate, PTFE, PEEK, and mixtures thereof. Other suitable materials include composites of e.g. ceramics, and mixtures thereof.

According to one embodiment, optical sensors may be arranged to measure the separation efficiency and particle size distribution. This could be monitored radially across the rotating discs to continuously obtain a density analysis of the fluid sample.

The invention also relates to the use of the monitoring system, particularly in large scale industrial separation units treating oil-water mixtures, process water such as pulp slurry, white water, and waste water; small miniaturised systems for e.g. separation of biological fluids, e.g. red blood cells from plasma, and other analytical sample work-up applications. Preferably, the separation apparatus is used to fractionate liquid-solid mixtures.

It has been found that the monitoring system as described herein is particularly suitable for separation of pulp and paper suspensions due to the relatively large density differences between fibres, fillers, and dissolved and colloidal substances (DCS) present in a paper furnish. The method enables e.g. characterisation of a sample, e.g. colloidal substances withdrawn from the outlet of the bore, e.g. pitch or stickies which contains substantially no extraneous fibrous and filler materials that influences the analysis result. While fibrous and filler materials can be removed, pitch and stickies are withdrawn from the bore. Pitch and stickies are detrimental to the paper machine operation and the content thereof must therefore be accurately monitored. Measurement of turbidity and total organic carbon (TOC) thereof can be carried out on a centrifuged sample. Since a turbidity analyser measures the amount of scattered light, present dissolved substances will not influence the measurement of pitch and stickies. The TOC analyser, however, measures the carbon content of all substances including the carbon content in present dissolved substances. To determine the content of stickies and pitch, the centrifuged sample must be further filtrated to remove pitch and stickies so that the amount of carbon in the dissolved substances can be determined. This is preferably carried out by filtration of the centrifuged sample through a filter membrane with a cutoff lower than about 0.1, preferably lower than about 0.01 μm. The amount of pitch and stickies can then be determined by subtracting the amount of carbon present in the filtered centrifuged sample from the total amount of carbon present in the centrifuged sample.

However, any other techniques of analysis may be employed depending on the type of centrifuged sample that is obtained. Such techniques include inter alia spectrophotometric analysis (including UV, Raman, visible, IR, NIR, and fluorescence), titration, electrochemical techniques (pH, conductivity), ion selective electrodes, pitch droplet counter or any optical method of sample characterisation (such as video camera and image analysis), liquid chromatography, gas chromatography, particle size analyzer (such as a Low Angle Laser Light Scattering) and/or in combination with further on-line sample work-up techniques such as filtration, distillation, liquid-liquid extraction etc.

However, the monitoring system and the above analysis techniques may also be used to separate and analyse any fractions of any fluid.

DESCRIPTION OF THE EMBODIMENTS

Figure 1:
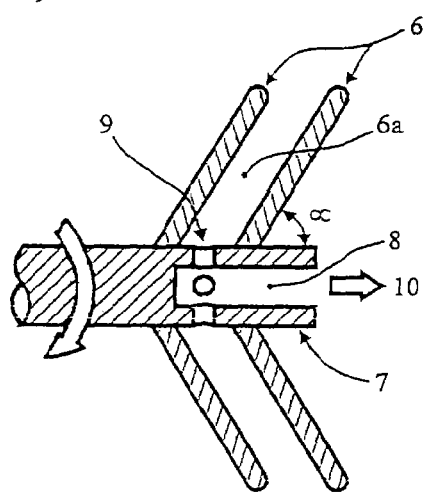
FIGS. 1a-d show different embodiments of the monitoring system.
Figure 1:
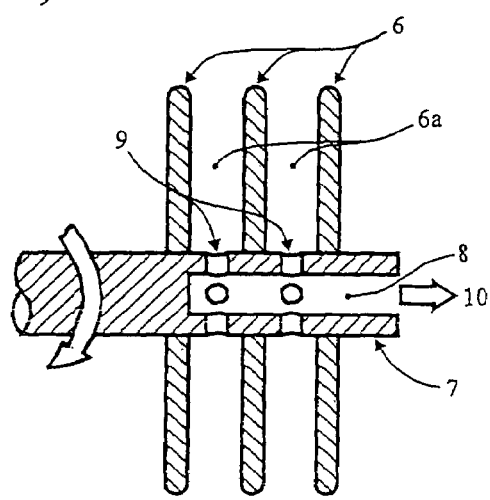
Figure 1:
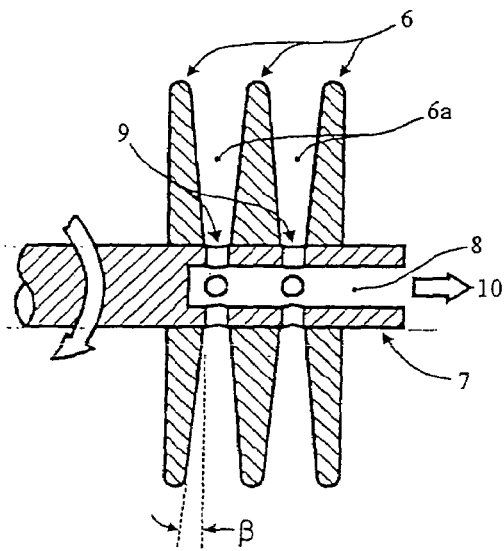
Figure 1:
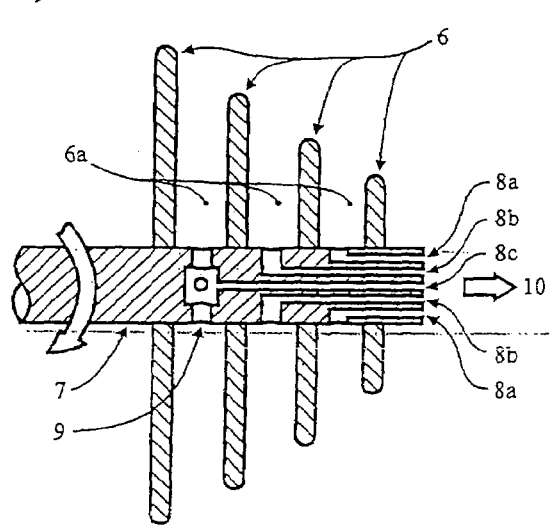

FIGS. 1a-d show embodiments of the separation apparatus (the analyser and further optional work-up equipment not shown) comprising rotating discs 6, defining spaces 6a between adjacent discs, arranged to a rotating axis 7 provided with at least one bore 8, 8a-c, apertures 9 enabling fluid communication between spaces 6a and the bore 8, 8a-c. The bore(s) 8, 8a-c comprise an outlet 10 through which a light fraction of a liquid fluid mixture supplied to the apparatus 16 can be withdrawn. FIG. 1a shows a disc arrangement in which the discs 6 form an angle $\beta$ to the axis 7. FIG. 1b shows a parallel arrangement between discs 6 perpendicular to axis 7. FIG. 1c shows inclined disc faces forming and angle $\beta$ between the face of adjacent discs. FIG. 1d shows discs 6 with increasing diameters. Spaces 6a fluidly communicate with separate bores 6a-c for withdrawal of separate density fractions from the separate spaces 6a.

Figure 2:
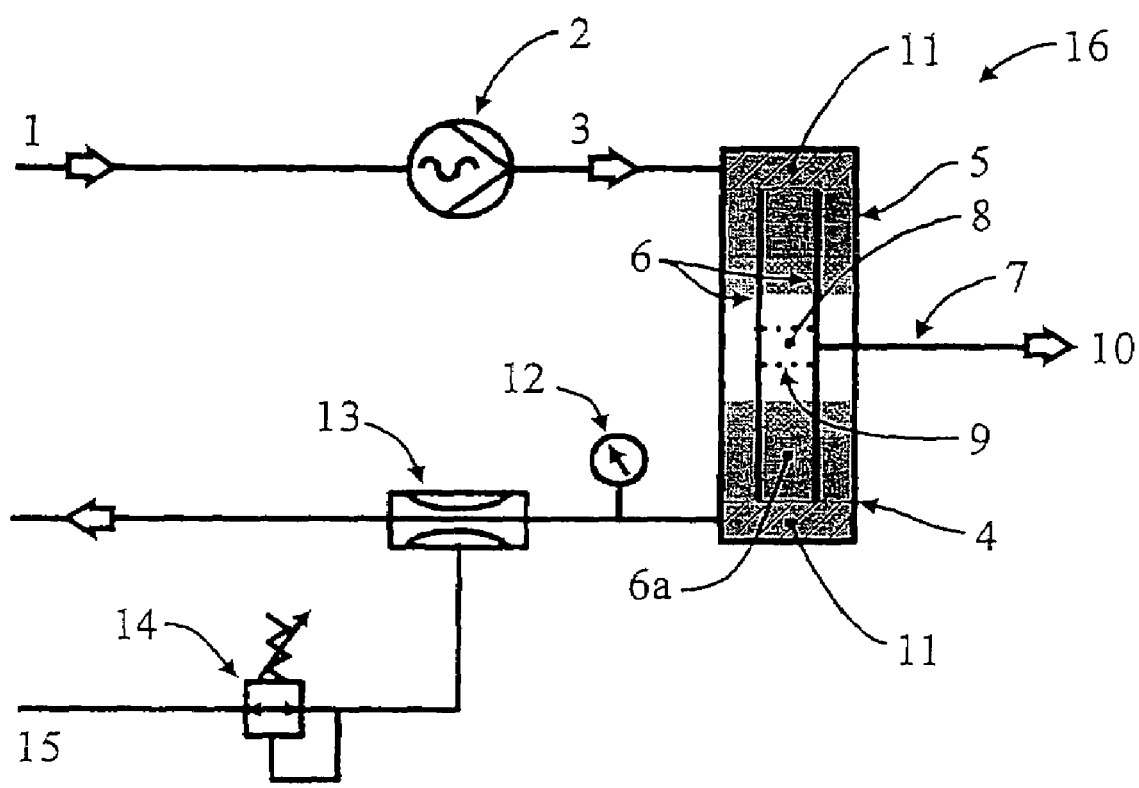
FIG. 2 shows a schematic view of the flow of fluid to a separation apparatus.

FIG. 2 shows feed of a liquid fluid mixture 1 to a pump 2 that pressurises 1 to obtain a pressurised liquid fluid mixture 3 that is supplied to the separation apparatus 16. The liquid fluid mixture 3 is supplied to the apparatus 16 through housing 5. 3 is directed to spaces 6a between rotating discs 6. As the discs 6 arranged to the axis 7 rotate, a centrifugal field of force is developed in the apparatus 16 that drags a dense fraction of 3 to the perimeter 11 thereof. A light fraction of 3 is pressed to the centre of the apparatus 16. Spaces 6a fluidly communicate with bore 8 through apertures 9 such that a light fraction of 3 can be withdrawn through an outlet 10, whereas a dense fraction of 3 can be withdrawn at the perimeter 4 through an outlet in the zone 11 (not shown). The dense fraction of 3 can then be remixed with feed 1 or used for other purpose. A pressure sensor 12 controls that a constant pressure is maintained in the apparatus 16. A valve 13, pressurised by external air 15, and regulator 14, are provided to regulate the existing pressure in the separation apparatus 16.

It will be obvious that the same may be varied in many ways, the invention being thus described. Such variations are not to be regarded as a departure from the gist and scope of the present invention, and all such modifications as would be obvious to one skilled in the art are intended to be included within the scope of the claims. The following example will further illustrate how the described invention may be performed without limiting the scope of it.

EXAMPLE 1

The experimental apparatus is shown in FIG. 2. The present system was evaluated on-line at a paper mill producing coated fine paper. Samples were taken continuously from the headbox at a consistency of approximately 7 g/L (total solids). The objective of this experiment was to investigate how two operational parameters, namely the rotational velocity of the discs ($\omega$) and the distance between the discs, have on the centrifuged sample quality taken out at point 10 (cf. FIG. 2). In order to monitor the "quality" of the centrifuged sample, a continuous in-line turbidity meter was utilised, measuring the turbidity of the centrifuged pulp sample at point 10.

| The following constant parameters were utilised: | |
|---|---|
| Number of discs | 2 |
| Bore diameter | 5 cm |
| Disc diameter | 20 cm |
| Disc material | surface hardened polycarbonate |
| Pulp (bulk) pressure | ca. 3.0 bar |
| Pulp (bulk) flow rate | ca. 6.2 L/min |
| Centrifuged sample flow rate | 200 mL/min (10% of inlet flow) |
| The following parameters were varied: | |
| Disc (motor) speed | 500-3000 rpm |
| Distance between the discs | 15 mm, 20 mm and 25 mm |

Figure 3:
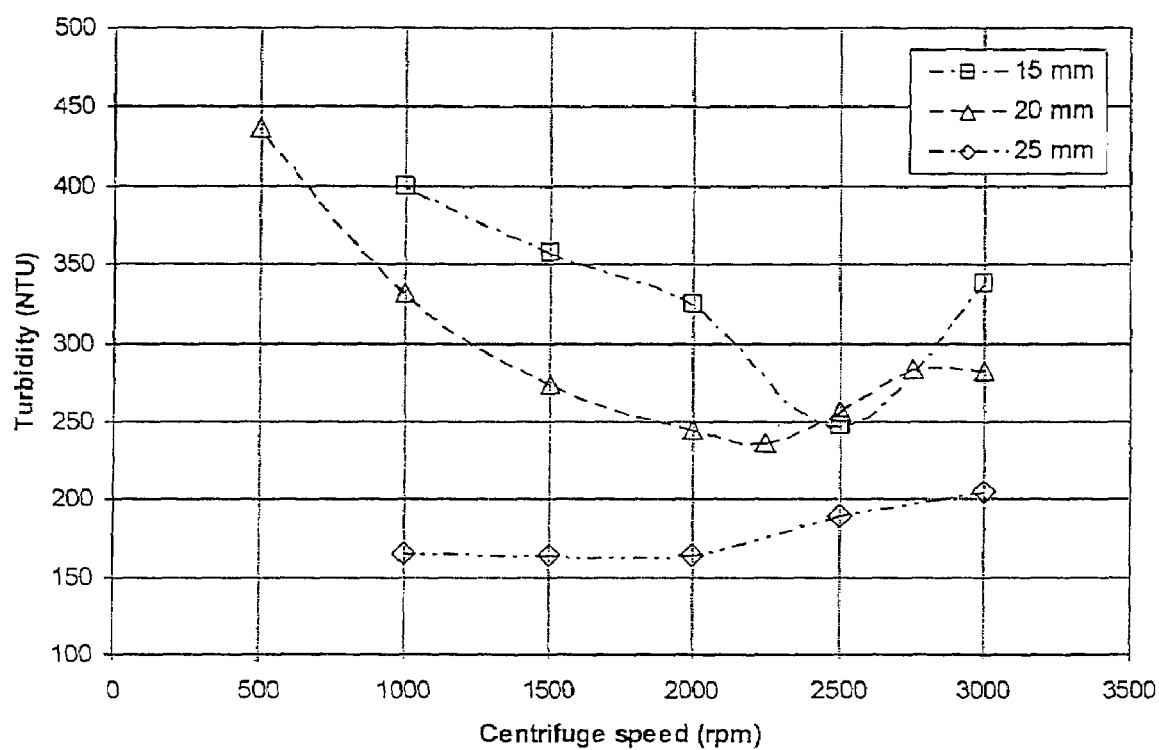
FIGS. 3 and 4 show results of turbidity and consistency measurements.

The results from the experiment are shown in FIG. 3. At each measurement point, the apparatus was run for approximately 15 minutes and an average of the turbidity values over this time was taken—in all cases the readings from the turbidity meter were stable (less than 5% variability). It must be noted however that some variability in our results is contributed to changes on the paper-machine (pulp furnish conditions) that we could not measure.

At all disc speeds between and including 500 rpm to 3000 rpm we did not notice the presence of wood fibres and/or fines in any of the obtained sample fractions (checked under a microscope). The variation in the turbidity values was related to the obtained distribution of residual coating and other materials often referred to as "stickies" and/or "macrostickies" at point 10. Since these materials have a density similar to water and are not necessarily colloidally stable, operational parameters were seen to influence the distribution of such substances. Further investigation, including laboratory centrifugation using similar g-forces obtained with the centrifuge (up to 3000 rpm, 30 minutes), did not appear to effect the distribution of the colloidally dispersed material, often referred to as "pitch".

EXAMPLE 2

The system as described in example 1 was operated continuously (24 hrs) and on-line at the same paper mill in order to measure process disturbances related to the presence of detrimental substances, referred to as "pitch" and "stickes". The apparatus used to measure changes in the pitch and stickies content was an in-line turbidity meter, as used in example 1, connected directly after the centrifuge on the centrifuged sample outlet. The same centrifuge conditions were utilised as in example 1, however with a constant disc speed of 2500 rpm and with a constant distance of 25 mm between the discs.

Figure 4:
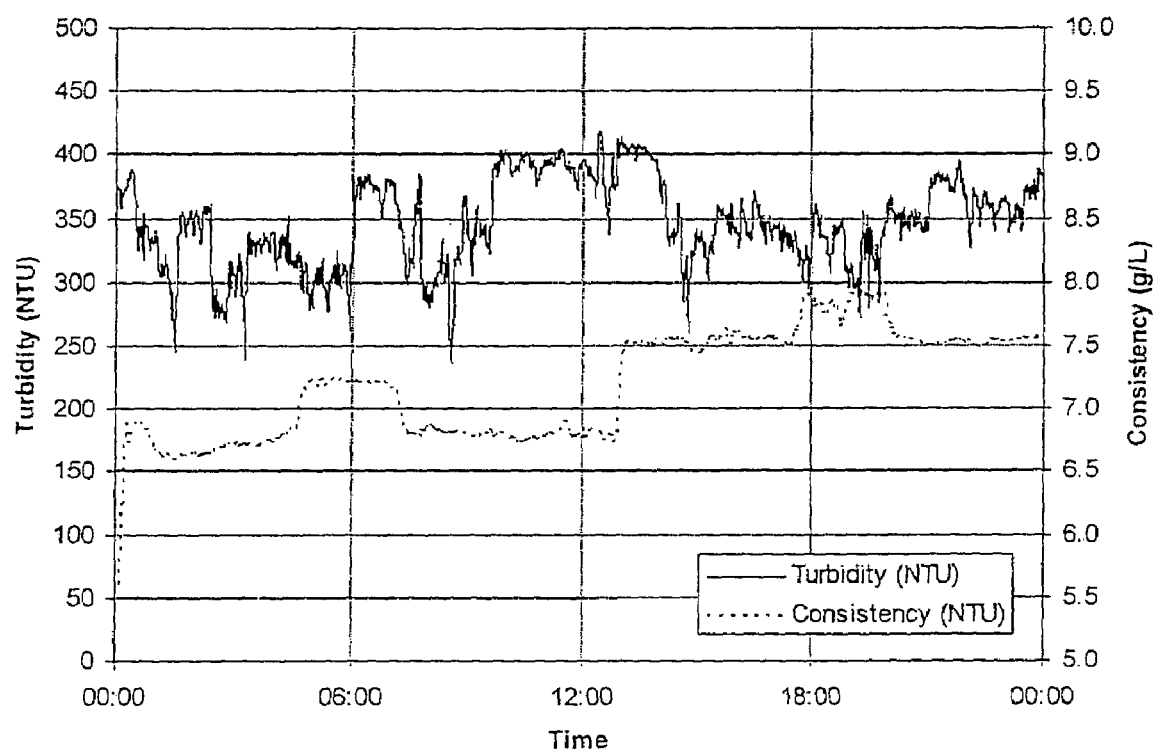

A 24 hour period of measurement data is shown in FIG. 4 along with data from a continuous pulp consistency measurement apparatus measuring the content of fines, fibres, and fillers. As can be seen from FIG. 4, the turbidity of the centrifuge sample is not necessarily dependent upon the consistency of the paper furnish. FIG. 4 also shows that all fines, fibres, and fillers are removed from the sample—otherwise the two curves would be identical. The availability of such turbidity data for the measurement of pitch and stickies has been valuable for troubleshooting paper machine disorders (poor runability) and has enabled dosage of chemical additives to be controlled in order to combat such problems.

The invention claimed is:

1. A method of monitoring a papermaking process comprising; withdrawing a liquid fluid mixture from a pulp suspension comprising fibrous and filler materials and colloidal substances; pressurising and supplying the liquid fluid mixture to a separation apparatus, said separation apparatus comprising at least two rotatable discs defining at least one space between the discs, means for withdrawing a dense fraction of the liquid fluid mixture from the perimeter of the discs, said discs being arranged to a rotatable axis defining within it at least one bore fluidly communicating with said at least one space, said at least one bore having at least one outlet for removing a light fraction of the liquid fluid mixture; subjecting the supplied pressurised liquid fluid mixture to centrifugal forces at said at least one space by rotating said at least two rotatable discs, such that a light fraction of the liquid fluid mixture is pressed to said at least one bore for withdrawal thereof, and a dense fraction of the liquid fluid mixture is pressed to the perimeter of the discs for withdrawal thereof; guiding said withdrawn light fraction to an analyser for characterisation thereof or at least one component therein to monitor a papermaking process.

2. A method according to claim 1, wherein about 0.0000001 to about 25% by volume of the liquid fluid mixture is withdrawn from the papermaking process and supplied, to the separation apparatus.

3. A method according to claim 1, wherein the withdrawn light fraction is further worked-up before being guided to the analyser.

4. A method according to claim 1, wherein the supplied liquid fluid mixture is pressurised by means of a pump.

5. A method according to claim 1, wherein the rotational speed is in a range such that laminar flow substantially prevails in the separation apparatus.

6. A method according to claim 1, wherein the rotational speed is from about 500 to about 10000 rpm.

7. A method according to claim 1, wherein the rotational speed is from about 1000 to about 5000 rpm.

8. A method according to claim 1, wherein the withdrawal of the dense fraction is made through an open perimeter of the discs.

9. A method according to claim 1, wherein from about 0.0000001 to about 25% by volume of a liquid fluid mixture is withdrawn from a paper production process and supplied to the separation apparatus.

10. A system comprising a papermaking machine and a monitoring system monitoring the operation of the papermaking machine, said monitoring system comprising a separation apparatus comprising at least two rotatable discs defining at least one space between said discs, means for pressurising and supplying a liquid fluid mixture to the separation apparatus, means for withdrawing a dense fraction of the liquid fluid mixture from the perimeter of the discs, said discs being arranged to a rotatable axis defining within it at least one bore fluidly communicating with said at least one space, said at least one bore having at least one outlet for withdrawing a light fraction of the liquid fluid mixture; said monitoring system further comprising an analyser connected to said separation apparatus to guide said light fraction from said outlet to said analyser.

11. A system according to any of claim 10, wherein the system comprises further working-up equipment connected to the system between outlet and the analyser.

12. A system according to any of claim 10, wherein the separation apparatus dues not comprise a housing.

13. A system according to claim 10, wherein the means of supplying and pressurising the liquid fluid mixture is a pump.

14. A method of monitoring the concentration of components of a colloidal solution containing cellulosic fibres in a system comprising pressurising and supplying a colloidal solution containing cellulosic fibres to a separation apparatus comprising at least two rotatable discs defining at least one space between said discs, means for pressurising and supplying the solution to the separation apparatus, means for withdrawing a dense fraction of the solution from the perimeter of the discs, said discs being arranged to a rotatable axis defining within it at least one bore fluidly communicating with said at least one space, said at least one bore having at least one outlet for withdrawing a light fraction of the solution; subjecting the supplied pressurised solution to centrifugal forces at said at least one space by rotating said at least two rotatable discs, such that a light fraction of the solution is pressed to said at least one bore for withdrawal thereof, and a dense fraction of the solution is pressed to the perimeter of the discs for withdrawal thereof; guiding said withdrawn light fraction to an analyser connected to said separation apparatus for characterisation thereof or at least one component therein.

* * * * *

UNITED STATES PATENT AND TRADEMARK OFFICE
CERTIFICATE OF CORRECTION

PATENT NO. : 7,311,848 B2  Page 1 of 1
APPLICATION NO. : 10/987183
DATED : December 25, 2007
INVENTOR(S) : M. Rice et al.

It is certified that error appears in the above-identified patent and that said Letters Patent is hereby corrected as shown below:

Title page,
Please insert the following related application information:

--Related U.S. Application Data--

Item --(60) Provisional application No. 60/519,634, filed on Nov. 14, 2003--

Claim 2, column 8, line 62
 "supplied, to the separation"   should read
 --supplied to the separation--  (delete the "," after supplied)

Claim 12, column 10, line 2
 "dues not comprise"   should read
 --does not comprise--  (change "dues" to "does")

Claim 14, column 10, line 24
 "thereof, and a dense"   should read
 --thereof and a dense--  (delete the "," after thereof)

Signed and Sealed this

Twenty-first Day of April, 2009

JOHN DOLL
*Acting Director of the United States Patent and Trademark Office*